(12) United States Patent
Kuo (10) Patent No.: US 7,648,360 B2
(45) Date of Patent: Jan. 19, 2010

(54) DENTAL APPLIANCE SEQUENCE ORDERING SYSTEM AND METHOD

(75) Inventor: Eric Kuo, Foster City, CA (US)

(73) Assignee: Align Technology, Inc., Santa Clara, CA (US)

( * ) Notice: Subject to any disclaimer, the term of this patent is extended or adjusted under 35 U.S.C. 154(b) by 1102 days.

(21) Appl. No.: 10/612,239

(22) Filed: Jul. 1, 2003

(65) Prior Publication Data

US 2005/0003319 A1    Jan. 6, 2005

(51) Int. Cl.
*A61C 3/00* (2006.01)
*A61B 19/02* (2006.01)

(52) U.S. Cl. .................. 433/6; 433/24; 206/63.5

(58) Field of Classification Search ............ 433/6, 433/24; 206/63.5, 534, 820; 221/22; 264/16–18
See application file for complete search history.

(56) References Cited

U.S. PATENT DOCUMENTS

| | | | |
|---|---|---|---|
| 1,508,095 A * | 9/1924 | Fuller | ............. 235/487 |
| 2,467,432 A | 4/1949 | Kesling | |
| 3,660,900 A | 5/1972 | Andrews | |
| 3,780,856 A * | 12/1973 | Braverman | ............. 206/534 |
| 3,860,803 A | 1/1975 | Levine | |
| 3,916,526 A | 11/1975 | Schudy | |
| 3,950,851 A | 4/1976 | Bergersen | |
| 4,014,096 A | 3/1977 | Dellinger | |
| 4,038,753 A * | 8/1977 | Klein | ............. 433/11 |
| 4,195,046 A | 3/1980 | Kesling | |
| 4,324,546 A | 4/1982 | Heitlinger et al. | |
| 4,348,178 A | 9/1982 | Kurz | |
| 4,478,580 A | 10/1984 | Barrut | |
| 4,504,225 A | 3/1985 | Yoshii | |
| 4,505,673 A | 3/1985 | Yoshii | |
| 4,575,805 A | 3/1986 | Moermann et al. | |
| 4,611,288 A | 9/1986 | Duret et al. | |
| 4,656,860 A | 4/1987 | Orthuber et al. | |
| 4,663,720 A | 5/1987 | Duret et al. | |
| 4,726,970 A * | 2/1988 | Morrish et al. | ............. 428/34.3 |
| 4,742,464 A | 5/1988 | Duret et al. | |

(Continued)

FOREIGN PATENT DOCUMENTS

DE    7411122 U    7/1974

(Continued)

OTHER PUBLICATIONS

Raintree Essix & ARS Materials, Inc., Raintree Essix Technical Magazine Table of Contents and Essix Applications, http://www.essix.com/magazine/default.html (Aug. 13, 1997) 7 pages.

(Continued)

*Primary Examiner*—John J Wilson
(74) *Attorney, Agent, or Firm*—Townsend and Townsend and Crew LLP (57) ABSTRACT

The present invention provides systems and methods for providing dental appliances, particularly orthodontic appliances, to a patient wherein the patient is easily able to determine the order or sequence in which the appliances should be worn. Typically the appliances are to be worn in a particular sequence to provide desired treatment, such as a progressive movement of teeth through a variety of arrangements to a final desired arrangement.

2 Claims, 7 Drawing Sheets

U.S. PATENT DOCUMENTS

| | | | |
|---|---|---|---|
| 4,755,139 A | 7/1988 | Abbatte et al. | |
| 4,763,791 A | 8/1988 | Halverson et al. | |
| 4,793,803 A | 12/1988 | Martz | |
| 4,798,534 A | 1/1989 | Breads | |
| 4,811,845 A * | 3/1989 | Baggett | 206/534 |
| 4,837,732 A | 6/1989 | Brandestini et al. | |
| 4,850,864 A | 7/1989 | Diamond | |
| 4,856,991 A | 8/1989 | Breads et al. | |
| 4,936,862 A | 6/1990 | Walker et al. | |
| 4,937,928 A | 7/1990 | Van Der Zel | |
| 4,964,770 A | 10/1990 | Steinbichler et al. | |
| 4,975,052 A | 12/1990 | Spencer et al. | |
| 5,011,405 A | 4/1991 | Lemchen | |
| 5,017,133 A | 5/1991 | Miura | |
| 5,027,281 A | 6/1991 | Rekow et al. | |
| 5,035,613 A | 7/1991 | Breads et al. | |
| 5,055,039 A | 10/1991 | Abatte et al. | |
| 5,059,118 A | 10/1991 | Breads et al. | |
| 5,100,316 A | 3/1992 | Wildman | |
| 5,121,333 A | 6/1992 | Riley et al. | |
| 5,128,870 A | 7/1992 | Erdman et al. | |
| 5,131,843 A | 7/1992 | Hilgers et al. | |
| 5,131,844 A | 7/1992 | Marinaccio et al. | |
| 5,139,419 A | 8/1992 | Andreiko et al. | |
| 5,184,306 A | 2/1993 | Erdman et al. | |
| 5,186,623 A | 2/1993 | Breads et al. | |
| 5,257,203 A | 10/1993 | Riley et al. | |
| 5,273,429 A | 12/1993 | Rekow et al. | |
| 5,278,756 A | 1/1994 | Lemchen et al. | |
| 5,326,259 A * | 7/1994 | Rohlcke et al. | 433/8 |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,411,295 A * | 5/1995 | Bates et al. | 283/81 |
| 5,431,562 A | 7/1995 | Andreiko et al. | |
| 5,440,496 A | 8/1995 | Andersson et al. | |
| 5,447,632 A | 9/1995 | Andersson | |
| 5,452,219 A | 9/1995 | Dehoff et al. | |
| 5,454,717 A | 10/1995 | Andreiko et al. | |
| 5,456,600 A | 10/1995 | Andreiko et al. | |
| 5,474,448 A | 12/1995 | Andreiko et al. | |
| 5,518,397 A | 5/1996 | Andreiko et al. | |
| 5,533,895 A | 7/1996 | Andreiko et al. | |
| 5,542,842 A | 8/1996 | Andreiko et al. | |
| 5,549,476 A | 8/1996 | Stern | |
| 5,587,912 A | 12/1996 | Andersson et al. | |
| 5,605,459 A | 2/1997 | Kuroda et al. | |
| 5,607,305 A | 3/1997 | Andersson et al. | |
| 5,645,421 A | 7/1997 | Slootsky | |
| 5,655,653 A | 8/1997 | Chester | |
| 5,683,243 A | 11/1997 | Andreiko et al. | |
| 5,733,126 A | 3/1998 | Andersson et al. | |
| 5,740,267 A | 4/1998 | Echerer et al. | |
| 5,882,192 A | 3/1999 | Bergersen | |
| 5,923,001 A * | 7/1999 | Morris et al. | 177/245 |
| 5,975,893 A | 11/1999 | Chishti et al. | |
| 6,206,695 B1 * | 3/2001 | Wong et al. | 433/102 |
| 6,884,071 B2 * | 4/2005 | Martin | 433/90 |
| 2003/0008259 A1 | 1/2003 | Shelton et al. | |
| 2003/0136698 A1 * | 7/2003 | Klatt | 206/499 |

FOREIGN PATENT DOCUMENTS

| | | | |
|---|---|---|---|
| DE | 3925088 A * | 1/1991 | |
| EP | 0091876 A1 | 10/1983 | |
| EP | 0299490 A2 | 1/1989 | |
| EP | 0376873 A2 | 7/1990 | |
| EP | 0490848 A2 | 6/1992 | |
| EP | 0774933 B1 | 5/1997 | |
| EP | 0541500 A1 | 6/1998 | |
| EP | 0731673 B1 | 9/1998 | |
| FR | 2369828 A1 | 6/1978 | |
| FR | 2652256 A1 | 3/1991 | |
| WO | WO 90/08512 A1 | 8/1990 | |
| WO | WO 91/04713 A1 | 4/1991 | |
| WO | WO 92/08419 | 5/1992 | |
| WO | WO 94/10935 A1 | 5/1994 | |
| WO | WO 98/44865 A1 | 10/1998 | |
| WO | WO 98/58596 A1 | 12/1998 | |

OTHER PUBLICATIONS

Chiappone, Constructing the Gnathologic Setup and Positioner, *J. Clin. Orthod.* 14:121-133 (1980).

Cottingham, Gnathologic clear plastic positioner, *Am. J. Orthodontics* 55:23-31 (1960).

Cureton, Correcting Malaligned Mandibular Incisors with Removable Retainers, *J. Clin. Orthodon.* 30:390-395 (1996).

Kessling, The Philosophy of the Tooth Positioning Appliance, *Am. J. Orthod Oral Surg.*, 31:297-304, (1945).

Kesling, Coordinating the Predetermined Pattern and Tooth Positioner with Conventional Treatment, *Am. J. Orthod. Oral Surg.*, 32: 285-293, (1946).

Kleeman et al., The Speed Positioner, *J. Clin. Orthod.* 30:673-680, (1996).

Shilliday, Minimizing finishing problems with the mini-positioner *Am. J. Orthod.* (1971) 59:596-599.

Warunek et al., Clinical use of silicone elastomer applicances *JCO* (1989) XXIII(10):694-700.

Wells, Application of the positioner appliance in orthodontic treatment *Am. J. Orthodont.* (1970) 58:351-366.

Alexander et al., "The DigiGraph Work Station Part 2, Clinical Management," *JCO* (Jul. 1990), pp. 402-407.

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures, " IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis," AADR Abstract #607,1980, 1 page total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A Stereophotogrammetric System for the Detection of Prosthesis Loosening in Total Hip Arthroplasty", NATO Symposium on Applications of Human Biostereometrics, Jul. 9-13, 1978, SPIE vol. 166, pp. 112-123.

Baumrind et al., Mapping the Skull in 3-D, Reprinted from The Journal, *California Dental Association*, vol. 48, No. 2 (1972 Fall Issue) 11 pages total.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. pp.142-166.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized Diagnosis in Orthodontics for Epidemiological Studies: A Progress Report", Abstracts of Papers, *Journal of Dental Research*; vol. 67, Special Issue Mar. 9-13, 1988, p. 169.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion In The Postcanine Dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Boyd et al., "Three Dimensional Diagnosis and Orthodontic Treatment of Complex Malocclusions Wlith the Invisalign Appliance", *Seminars in Orthodontics*, vol. 7, No. 4 (Dec. 2001), p. 274-293.

Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.

Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.

Burstone (interview), "Dr. Charles J. Burstone on The Uses of the Computer in Orthodontic Practice (Parts 1 and 2)," *Journal of Clinical Orthodontics*, (Part 1) vol. 8, No. 7, Jul. 1979; (Part 2) vol. 8, No. 8 pp. 539-551, Aug. 1979.

Burstone et al., "Precision Adjustment of the Transpalatal Lingual Arch: Computer Arch Form Predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bites" The Computer Moves From The Front Desk To The Operatory, *Canadian Dental Journal*, vol. 54(9), , (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

Defranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 2 pages total.

DenTrac Corporation, Dentrac document, pp. 4-13.

Duret et al, "CAD-CAM in Dentistry," *Journal of the American Dental Association*, vol. 117 (Nov. 1988), pp. 715-720.

Duret et al., "CAD/CAM Imaging in Dentistry," *Current Opinion in Dentistry*, vol. 1 (1991), pp. 150-154.

Duret, "Vers une prosthese informatisee," (English translation also attached), *Tonus*, vol. 75, (Nov. 15, 1985), pp. 55-57.

Duret, "The Dental CAD/CAM, General Description of the Project," *Hennson International Product Brochure*, Jan. 1986., 18 pages total.

Economides, "The Microcomputer in the Orthodontic Office," *JCO*, (Nov. 1979), pp. 767-772.

Elsasser, "Some Observations on the History and Uses of the Kesling Positioner" *Am. J. Ortho.*, vol. 36, No. 5, (May 1950) pp. 368-374.

Faber et al.,"Computerized Interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery,"Abstract of Papers, *Journal of Dental Research*, vol. 70 (1987), pp. 754-760.

Gim-Alldent Deutschland, "Das DUX System: Die Technik" 2 pages total.

Grayson, "New Methods for Three Dimensional Analysis of Craniofacial Deformity," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxilofacial Surgery*, vol. 48, No. 8, Supp. 1, Aug. 1990, p. 5-6.

Guess et al., "Computer Treatment Estimates in Orthodontics and Orthognathic Surgery," *JCO* (Apr. 1989), pp. 262-328.

Heaven et al., "Computer-based Image Analysis of Artificial Root Surface Caries," Abstracts of Papers, *Journal of Dental Research*, vol. 70,Apr. 17-21, 1991, p. 528.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

JCO Interviews, "Craig Andreiko , DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The Problem, Electronic Data Transmission and the Law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners With LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.* , vol. 63, No. 11 (Nov. 1984), pp. 1298-1301.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

Manetti et al., "Computer-aided Cefalometry and New Mechanics in Orthodontics" (Article Summary in English, article in German), *Fortschr. Kieferorthop*. 44, 370-376 (Nr. 5), 1983.

McCann, Inside the ADA, *Journal Of The American Dental Assoc.*, vol. 118 (Mar. 1989) pp. 286-294.

McNamara et al., "Invisible Retainers", *J. Clinical Orthodontics*, (Aug. 1985) pp. 570-578.

McNamara et al., Chapter 19: Invisible Retainers, *Orthodontic and Orthopedic Treatment in the Mixed Dentition*, Needham Press, Jan. 1993. pp. 347-353.

Moermann et al., "Computer Machined Adhesive Porcelain Inlays: Margin Adaptation after Fatigue Stress," IADR Abstract 339, *Journal of Dental Research*, vol. 66(a) (1987), p. 763.

Mörmann et al., "Marginal Adaptation von adhasiven Porzellaninlays in vitro,"*Schwizerische Monatsshrift fur Zahnmedizin*, vol. 85 (1985), p. 1118-1129.

Nahoum, "The Vacuum Formed Dental Contour Appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

Nishiyama at al., "A New Construction Of Tooth Repositioner By LTV Vinyl Silicone Rubber" J. Nihon University School of Dentistry, 19(2):93-102, 1977.

Pinkham, "'Foolish' Concept Propels Technology," *Dentist*, Jan./Feb. 1989, 3 pages total.

Pinkham, "Inventor's CAD/CAM may transform dentistry," *Dentist*, Sep. 1990, 3 pages total.

Ponitz,"Invisible Retainers", *Am. J. Orthodontics*, vol. 59, No. 3, Mar. 1971, pp. 266-272.

Procera Research Projects, *PROCERA Research Projects 1993—Abstract Collection*, 1993, pp. 3-24.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, "Feasibility of an Automated System for Production of Dental Restorations," PhD Thesis, Univ. of Minnesota, Nov. 1988, 244 pages total.

Richmond et al., Research Reports, "The Development of a 3D Cast Analysis System," *British Journal of Orthodontics*, vol. 13, No. 1, (Jan. 1986) pp. 53-54.

Richmond, "Recording The Dental Cast In Three Dimensions," *Am. J. Orthod. Dentofac. Orthop.*, vol. 92, No. 3, (Sep. 1987), pp. 199-206.

Rudge, "Dental arch analysis: arch form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computed Tomography in Maxillofacial Surgical Planning," *Arch Otolamgol Head Neck Surg.* vol. 114 (Apr. 1988), pp. 438-442.

Siemens, "CEREC—Computer-Reconstruction,"High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050342, filed Jun. 20, 1997, 41 pages total.

Van Der Linden et al., "Three-Dimensional Analysis of Dental Casts by Means of the Optocom," *J Dent Res*, Jul.-Aug. 1972, vol. 51, No. 4, p. 1100.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Várady et al., 37 Reverse engineering of geometric models—an introduction. Computer-Aided Design, 29 (4):255-268, 1997.

Warunek et al., "Physical And Mechanical Properties of Elastomers In Orthodontic Positioners" *Am. J. Orthod. Dentofac. Orthop.*, 95:388-400, 1989.

Williams, "Dentistry and CAD/CAM: Another French Revolution,"*Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis Of Three-Dimensional Tooth Movement in Orthodontics," *Frontiers in Med. and Biol. Eng'g*, vol. 1, No. 2 (1988), pp. 119-130.

"Important Tip About Wearing the Red White & Blue Active Clear Retainer System," Allesee Orthodontic Appliances-Pro Lab, 1 page.

"The Choice Is Clear: Red, White & Blue . . . The Simple, Affordable, No-Braces Treatment," Allesee Orthodontic Appliances-Pro Lab product information for doctors, <http://ormco.com/aoa/appliancesservices/RWB/doctor.html>, 5 pages (May 19, 2003).

"The Choice is Clear: Red, White & Blue . . . The Simple, Affordable, No-Braces Treatment," Allesee Orthodontic Appliances-Pro Lab product information for patients, <http://ormco.com/aoa/appliancesservices/RWB/patients.html>, 2 pages (May 19, 2003).

"The Choice Is Clear: Red, White & Blue . . . The Simple, Affordable, No-Braces Treatment," Allesee Orthodontic Appliances-Pro Lab product information, 6 pages (2003).

"The Red, White & Blue Way to Improve Your Smile!" Allesee Orthodontic Appliances-Pro Lab product information for patients, 2 pages.

"You May Be A Candidate For This Invisible No-Braces Treatment," Allesee Orthodontic Appliances-Pro Lab product information for patients, 2 pages.

DuraClear™ product information, Allesee Orthodontic Appliances-Pro Lab, 1 page.

Moles, Randall C., "Correcting Mild Malalignments—as Easy as One, Two, Three," *AOA/Pro Corner*, 2 pages.

U.S. Appl. No. 11/285,707, for "Dental Appliance Sequence Ordering System and Method," by Eric E. Kuo.

* cited by examiner

DENTAL APPLIANCE SEQUENCE ORDERING SYSTEM AND METHOD

STATEMENT AS TO RIGHTS TO INVENTIONS MADE UNDER FEDERALLY SPONSORED RESEARCH OR DEVELOPMENT

NOT APPLICABLE

CROSS-REFERENCES TO RELATED APPLICATIONS

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

1. Field of the Invention

The present invention is related generally to the field of orthodontics. More particularly, the present invention is related to methods and systems for dispensing a series of orthodontic appliances in a sequence to a patient.

Repositioning teeth for aesthetic or other reasons is accomplished conventionally by wearing what are commonly referred to as "braces." Braces comprise a variety of appliances such as brackets, archwires, ligatures, and O-rings. Attaching the appliances to a patient's teeth is a tedious and time consuming enterprise requiring many meetings with the treating orthodontist. Consequently, conventional orthodontic treatment limits an orthodontist's patient capacity and makes orthodontic treatment quite expensive. Moreover, from the patient's perspective, the use of braces is unsightly, uncomfortable, presents a risk of infection, and makes brushing, flossing, and other dental hygiene procedures difficult.

As a result, alternative methods and systems for repositioning teeth have been developed. For example, repositioning may be accomplished with a system comprising a series of appliances configured to receive the teeth in a cavity and incrementally reposition individual teeth in a series of at least three successive steps. Most often, the methods and systems reposition teeth in from ten to twenty-five successive steps, although complex cases involving many of the patient's teeth may take forty or more steps. The individual appliances are typically comprised of a polymeric shell having the teeth-receiving cavity formed therein, typically by molding. The successive use of a number of such appliances permits each appliance to be configured to move individual teeth in small increments.

Typically the systems are planned and all individual appliances are fabricated at the outset of treatment. Thus, the appliances may be provided to the patient as a single package or system. The order in which the appliances are to be used can be marked by sequential numbering directly on the appliances or on tags, pouches or other items which are affixed to or which enclose each appliance so that the patient can place the appliances over his or her teeth in an order and at a frequency prescribed by the orthodontist or other treating professional. Successive appliances will be replaced when the teeth either approach (within a preselected tolerance) or have reached the target end arrangement for that stage of treatment, typically being replaced at an interval in the range from 2 days to 20 days, usually at an interval in the range from 5 days to 10 days.

In general, it is preferable to simplify procedures for the patient to increase patient compliance and reduce patient errors in carrying out the treatment protocol. Therefore, it is desirable to utilize a packaging or ordering system which will provide appliances to a patient in a manner which is clearly discernable to the patient the order of the appliances. In addition, such packaging or ordering system should be amenable to mid-treatment changes to the treatment protocol, possibly adding or eliminating appliances after the initial set of appliances has been produced and packaged. At least some of these objectives will be met by the methods and systems of the present invention described hereinafter.

2. Description of the Background Art

Tooth positioners for finishing orthodontic treatment are described by Kesling in the *Am. J. Orthod. Oral. Surg.* 31:297-304 (1945) and 32:285-293 (1946). The use of silicone positioners for the comprehensive orthodontic realignment of a patient's teeth is described in Warunek et al. (1989) *J. Clin. Orthod.* 23:694-700. Clear plastic retainers for finishing and maintaining tooth positions are commercially available from RAINTREE ESSIX, INC., New Orleans, La. 70125, and TRU-TAIN PLASTICS, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139.

Other publications describing the fabrication and use of dental positioners include Kleemann and Janssen (1996) *J. Clin. Orthodon.* 30:673-680; Cureton (1996) *J. Clin. Orthodon.* 30:390-395; Chiappone (1980) *J. Clin. Orthodon.* 14:121-133; Shilliday (1971) *Am. J. Orthodontics* 59:596-599; Wells (1970) *Am. J. Orthodontics* 58:351-366; and Cottingham (1969) *Am. J. Orthodontics* 55:23-31.

BRIEF SUMMARY OF THE INVENTION

The present invention provides systems and methods for providing dental appliances, particularly orthodontic appliances, to a patient wherein the patient is easily able to determine the order or sequence in which the appliances should be worn. Typically the appliances are to be worn in a particular sequence to provide desired treatment, such as a progressive movement of teeth through a variety of arrangements to a final desired arrangement.

In a first aspect of the present invention, a system of dental appliances is provided comprising a plurality of dental appliances wherein at least some of the plurality include a non-numeric indicia designating an order in which each of the at least some of the plurality are to be worn by a patient to provide dental treatment. Typically, each of the plurality of dental appliances comprise a polymeric shell having cavities shaped to receive and resiliently reposition teeth from one arrangement to a successive arrangement. Exemplary embodiments of such dental appliances are described in U.S. Pat. No. 5,975,893, incorporated herein by reference for all purposes. In some embodiments, each of the polymeric shells has at least one terminal tooth cavity and the indicia comprises a terminal tooth cavity of differing length in each of the polymeric shells. In other embodiments, each of the polymeric shell has a height and the indicia comprises a different height in each of the polymeric shells.

In still other embodiments, the indicia comprises one or more cutouts so that each polymeric shell has a different cutout pattern. Sometimes the cutout comprises a notch in an edge of the appliance.

In yet other embodiments, the indicia comprises a color wherein each appliance has different color. The color of the appliances may have the same hue and vary by intensity, for example. The color may comprise a dissolvable dye. Or, the system may further comprise a wrapper removably attachable to each of the appliances, wherein each wrapper has the color.

In another aspect of the present invention, a system of packaged dental appliances is provided comprising a plurality of packages each containing a dental appliance, wherein the plurality of packages are joined in a continuous chain designating an order in which each of the dental appliances are to be worn by a patient to provide dental treatment. In some instances, the packages are each joined by a perforation wherein the packages can be separated by breaking the perforation. In other instances, the packages are joined by, for example, a heat seal. Further, the system may include a marking on a package at an end of the chain indicating the dental appliance to be worn first. Again, each of the plurality of dental appliances may comprise a polymeric shell having cavities shaped to receive and resiliently reposition teeth from one arrangement to a successive arrangement.

In a further aspect of the present invention, a system of dental appliances is provided comprising a plurality of dental appliances to be worn by a patient to provide dental treatment, and a framework, wherein each of the plurality of dental appliances are removably attached to a portion of the framework. In some embodiments, each of the plurality of dental appliances comprise a polymeric shell having cavities shaped to receive and resiliently reposition teeth from one arrangement to a successive arrangement. Further, the system may comprise at least one marking on the framework indicating the order in which the appliances are to be worn by a patient.

In still another aspect of the present invention, method of dispensing dental appliances to a patient is provided. The method including the step of providing a plurality of packages wherein each of the packages includes a polymeric shell having cavities shaped to receive and resiliently reposition teeth from one arrangement to a successive arrangement, the plurality of package including a first package containing a first shell to be worn by the patient to reposition the teeth from the one arrangement to the successive arrangement and a second package containing a second shell to be worn by the patient to reposition the teeth from the successive arrangement to another successive arrangement. The method further including the steps of delivering the first package to the patient at a designated time through a remote delivery system, and delivering the second package to the patient at a later designated time through the remote delivery system. In most embodiments, the remote delivery system comprises a mail delivery system.

In another aspect of the present invention, a method is provided of dispensing dental appliances to a patient including providing a dispenser including a plurality of dental appliances, wherein each of the appliances comprises a polymeric shell having cavities shaped to receive and resiliently reposition teeth from one arrangement to a successive arrangement, the plurality of appliances including a first shell to be worn by the patient to reposition the teeth from the one arrangement to the successive arrangement and a second shell to be worn by the patient to reposition the teeth from the successive arrangement to another successive arrangement, and removing the first shell from the dispenser wherein removal of the first shell dispenses the second shell.

In a further aspect of the present invention, a method of dispensing dental appliances to a patient is provided including providing a dispenser including a plurality of dental appliances, wherein each of the appliances comprises a polymeric shell having cavities shaped to receive and resiliently reposition teeth from one arrangement to a successive arrangement, the plurality of appliances including a first shell to be worn by the patient to reposition the teeth from the one arrangement to the successive arrangement and a second shell to be worn by the patient to reposition the teeth from the successive arrangement to another successive arrangement. The method further includes removing the first shell from the dispenser, and actuating an actuator that subsequently dispenses the second shell. In most embodiments, the actuator comprises a lever, knob, or button.

DETAILED DESCRIPTION OF THE INVENTION

It may be appreciated that the orthodontic appliances may be dispensed to the patient in its entirety, in groups or individually. Providing the patient with the entire series at the outset of treatment may be desirable if the treatment plan is relatively short, the patient is particularly compliant, or it is particularly convenient, to name a few. In this case, the series should be ordered so that the patient can easily selected the next appliance in the sequence when needed. Such ordering may be designated through packaging or the appliance itself. In some situations, the patient may receive additional appliances during the treatment protocol for inclusion in the sequence and/or the patient may receive instructions to eliminate some of the original appliances from the treatment protocol. Therefore, such ordering should allow easy incorporation of additional appliances or deletion of appliances.

Alternatively, the patient may be provided with a subset of the entire series, such as the first ten appliances. In this case, the subset should be ordered so that the patient can easily selected the next appliance in the sequence when needed. Again, such ordering may be designated through packaging or the appliance itself. The patient may receive additional appliances during the use of the subset for inclusion in the sequence and/or the patient may receive instructions to eliminate some of the original appliances from the subset. Alternatively, the next subset of appliances may differ from that which was initial determined at the outset of the treatment protocol. Therefore, such ordering should allow easy incorporation of additional appliances or deletion of appliances within or between subsets.

Further, the patient may be provided with individual appliances in the order in which they should be used. In this case, the appliances should be ordered so that the patient can easily differentiate the appliance they are receiving from the appliances already received. Again, such ordering may be designated through packaging or the appliance itself. In addition, such ordering should allow the appliances to be stored and distributed to the patient in the correct sequence with minimal attention from the orthodontic practitioner.

Figure 1:
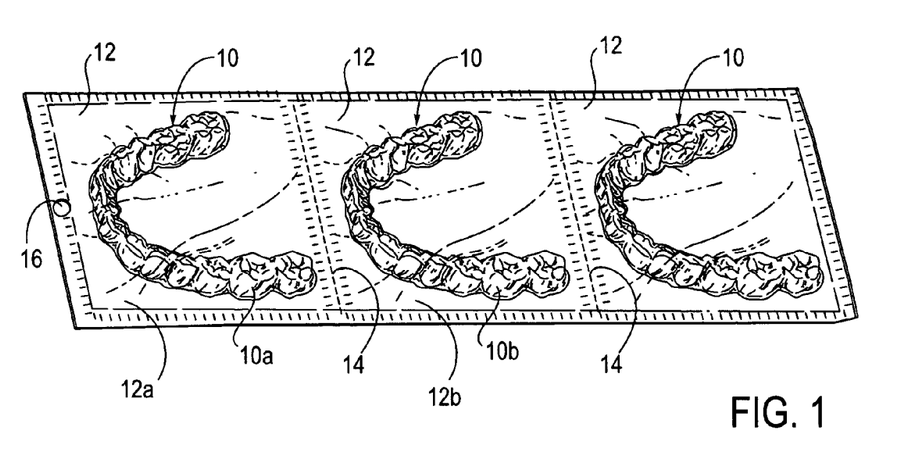
FIG. 1 is a schematic illustration of a series of appliances dispensed in a chain.

A variety of embodiments of ordering systems and methods will be described. In a first embodiment, a series of appliances are dispensed to the patient in a continuous chain, wherein the appliances are to be used in the sequence of the chain. An example of such a chain is schematically illustrated in FIG. 1. Here, each appliance 10 is disposed within a package 12, wherein the packages 12 are joined together in a continuous chain. In this embodiment, each package 12 is separable at a perforation 14 from the remaining packages 12 in the chain. It may be appreciated that the packages may be joined and/or are separable in any suitable manner including with the use of adhesives, heat sealing, ultrasonic welding, linkages or simply indications where to cut, break or separate, to name a few. To indicate the end of the chain in which it begin use, a marking may be located on the package 12 or on the appliance 10. For example, a colored marking 16 may be located on an end package 12a, as shown. This would indicate that a first appliance 10a is enclosed. Once the first appliance 10a has been removed from the package 12a and worn for a given amount of time, the patient may then open a next package 12b in the chain and remove a second appliance 10b for wearing. This may be repeated throughout the chain.

Figure 2:
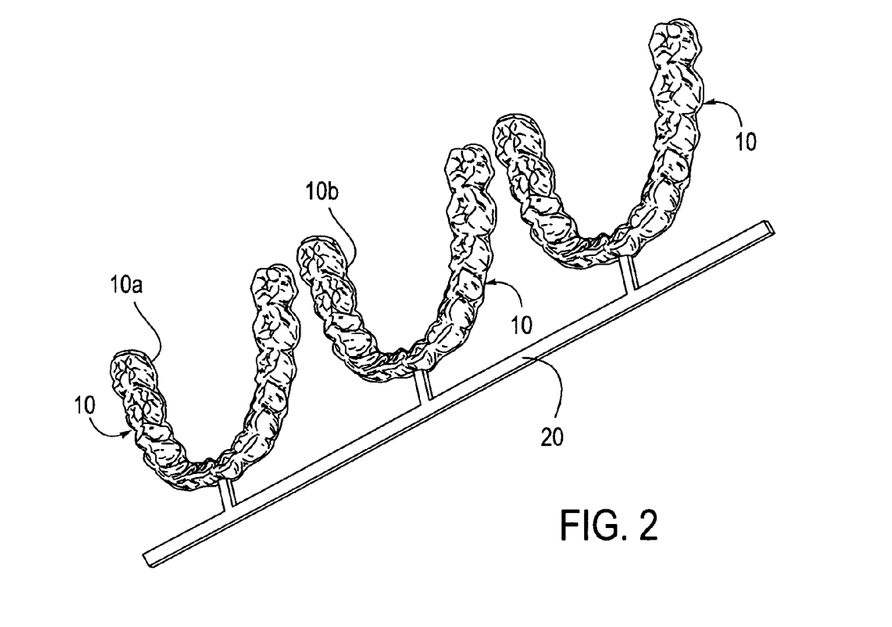
FIG. 2 illustrates a series of appliances disposed on a framework.

In another embodiment, illustrated in FIG. 2, a series of appliances 10 are disposed on a framework 20, such as a sprue. Sprues typically secure objects, such as molded objects, before their first use. The appliances 10 are secured to the framework 20 in any suitable manner. The appliances 10 are then removed from the framework 20 according to a the treatment protocol. For example, the first appliance 10a to be used may be disposed at one end of the framework 20, the second appliance 10b disposed next to the first appliance 10a, the sequence continuing along the framework 20. Alternatively or in addition, markings may be disposed on the framework 20 or the appliances 10 themselves indicating an ordering of use.

Figure 3:
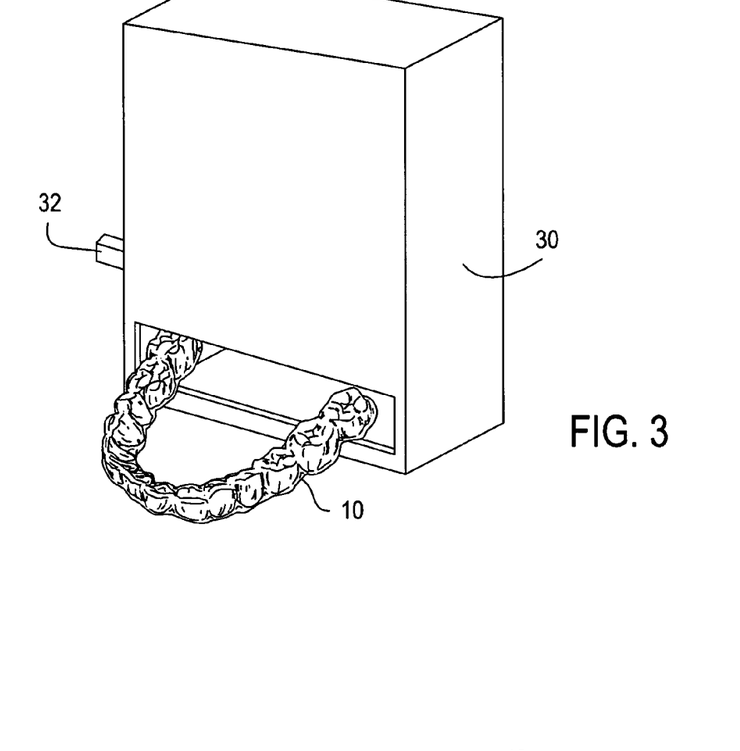
FIG. 3 illustrates a series of appliances provided to a patient in a dispenser.

In another embodiment, illustrated in FIG. 3, a series of appliances 10 are provided to a patient in a dispenser 30. The dispenser 30 dispenses the appliances 10 in the order to be used. Each appliance 10 may be individually dispensed, as shown, or each appliance 10 may be contained in a package wherein the packages are individually dispensed. The dispenser 30 may include an actuator 32, such as a lever, button, switch, etc, so that actuation of the actuator 32 dispenses the appliance 10 or package containing the appliance 10. Alternatively, removal of an appliance 10 from the dispenser 30 may actuate dispensing of the next appliance 10. In this way, the patient is systematically dispensed appliances in a predetermined order of use.

Figures 4A, 4B:
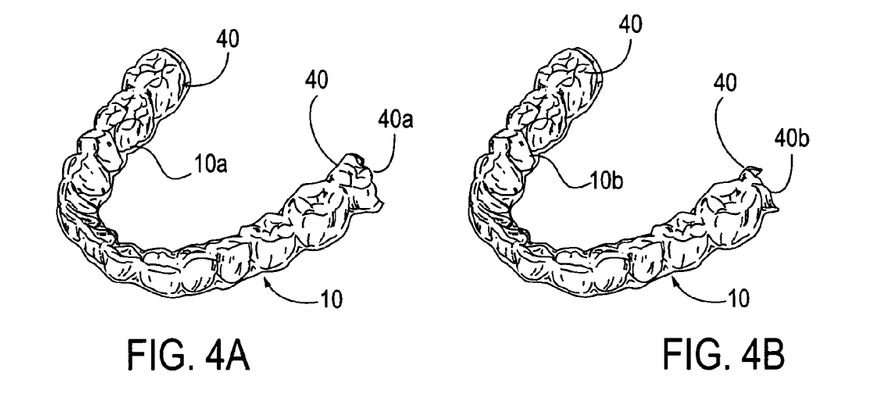
FIGS. 4A-4B illustrate a change in length of a terminal tooth cavity between appliances in a series.

In some situations it may be desired to specifically mark the appliances themselves. Such markings ensure that ordering of the appliances is distinguishable after removal of the appliances from any packaging and during use. For example, a portion of each appliance may be changed to indicate a sequence or order. FIGS. 4A-4B illustrate a change in length of the appliance 10 by changing the length of a terminal tooth cavity 40. A terminal tooth cavity 40 is one of the last teeth in the appliance. FIG. 4A illustrates a first appliance 10a wherein a marked terminal tooth cavity 40a has a given length. FIG. 4B illustrates a second appliance 10b wherein a marked terminal tooth cavity 40b has a length which differs from the first appliance 10a. Here, the marked terminal tooth cavity 40b has a shorter length. The lengths can continue to differ throughout the sequence of appliances. Alternatively or in addition, the lengths of other terminal teeth may differ.

Figure 5A:
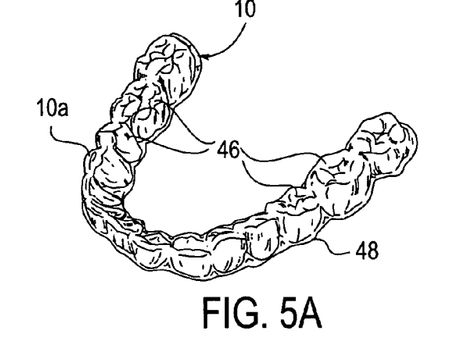
FIGS. 5A-5B illustrate a change in height between appliances in a series.
Figure 5B:
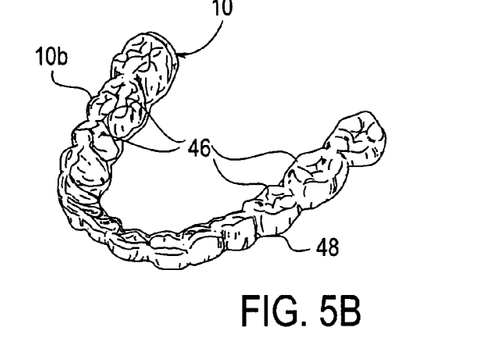

FIGS. 5A-5B illustrate a change in the height of each appliance 10 to indicate a sequence or order. The height of the appliance 10 is the distance from the occlusal surfaces 46 to the edges 48 of the appliance 10. FIG. 5A illustrates a first appliance 10a having a given height. FIG. 5B illustrates a second appliance 10b having a height which differs from the first appliance 10a. Here, the second appliance 10b has a shorter height. The heights can continue to differ throughout the sequence of appliances indicating an order. It may be appreciate that the overall height of the appliance may differ or the height of specific portions of the appliance may differ through the sequence.

Figure 6A:
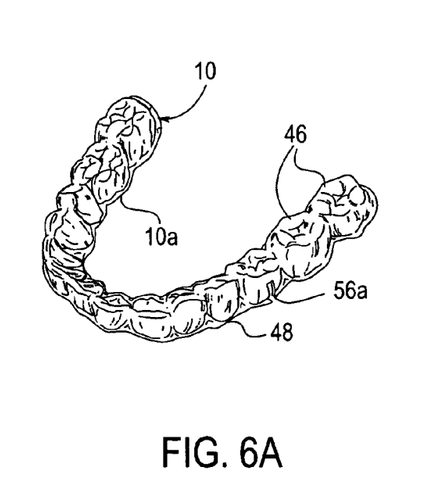
FIGS. 6A-6B illustrate the addition of cutouts in each appliance to indicate an order.
Figure 6B:
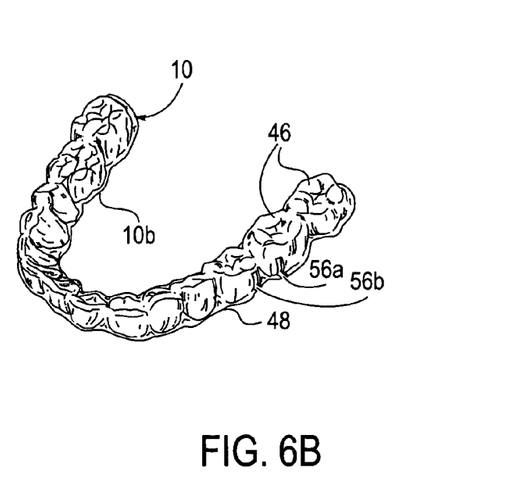

FIGS. 6A-6B illustrate the addition of notches or cutouts 56 in each appliance 10 to indicate a sequence or order. The cut outs may be of any size, shape, orientation, or number forming any pattern. Further, the cut outs may be located on an edge 48 of the appliance 10 or on any surface, including an occlusal surface 46. FIG. 6A illustrates a first appliance 10a having a first cut out 56a. The first cut out 56a has a rectangular shape and is located near an edge 48. FIG. 5B illustrates a second appliance 10b having a second cut out 56b so that the cut out pattern of the first appliance 10a differs from that of the second appliance 10b. Here, the second cut out 56b also has a rectangular shape and is located near the edge 48 adjacent to the first cut out 56a. The cut out patterns can continue to differ throughout the sequence of appliances indicating an order.

Figure 7A:
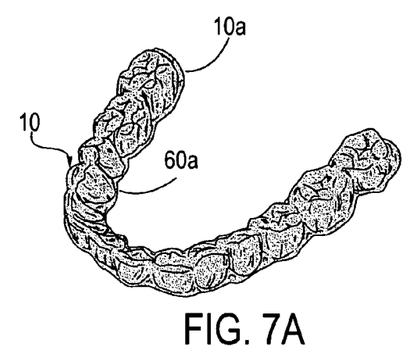
FIGS. 7A-7C illustrate a change in color to indicate an order.
Figure 7B:
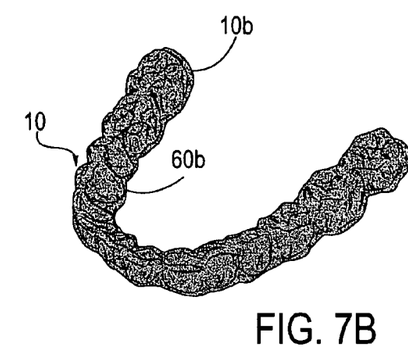
Figure 7C:
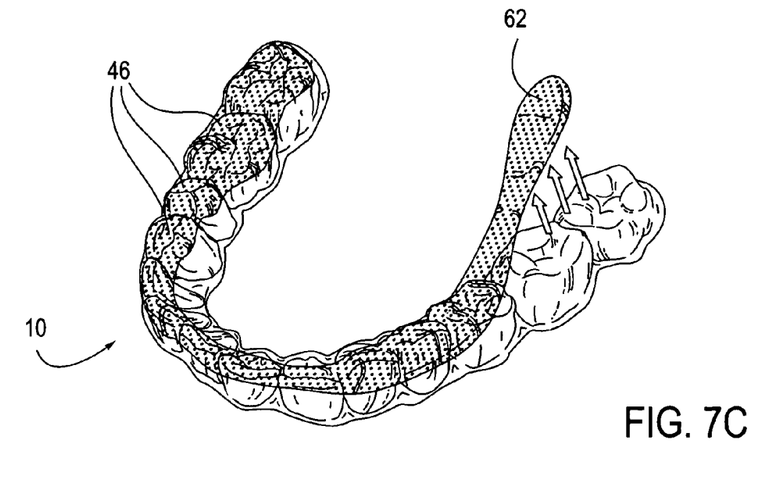

FIGS. 7A-7C illustrate a change in color, such as a hue, gradation of hues, shade, tint or intensity, for each appliance 10 to indicate a sequence or order. For example, the appliances 10 may appear darker or lighter in color through the series, such as ranging from dark red to light pink or vice versa. Or, the sequence may follow the color of the rainbow, such as red, orange, yellow, green, etc. Or, the sequence may follow any other prescribed order of colors. FIG. 7A illustrates a first appliance 10a having a first color 60a. FIG. 7B illustrates a second appliance 10b having a second color 60b so that the color of the first appliance 10a differs from that of the second appliance 10b. The color changes can continue to differ throughout the sequence of appliances indicating an order. It may be appreciated that the appliances 10a, 10b may have the color over their entirety, as shown, or the appliances may be colored in some areas and not in others. Or multiple colors may be used on a single appliance, such as in stripes, blocks or various shapes. The color may be embedded in the appliance, such as with the use of a colored plastic rather than the typical clear plastic. Or, the color may be in the form of a dissolvable dye which dissolves in contact with air, such as upon removal from a package, or contact with liquid, such as when rinsed with water or placed in the patient's mouth. Alternatively, as illustrated in FIG. 7C, the color may be present in a peel-away wrapper 62. The colored wrapper 62 may be attached to the appliance 10 by lamination or other methods. In this example, the wrapper 62 covers the occlusal surfaces 46 of the appliance 10, however any portion of the appliance 10 may be covered. When the appliance 10 is to be used, the wrapper 62 is peeled away, as shown, and removed. In this way, the appliances may be ordered by color but worn in a transparent state.

Figure 8:
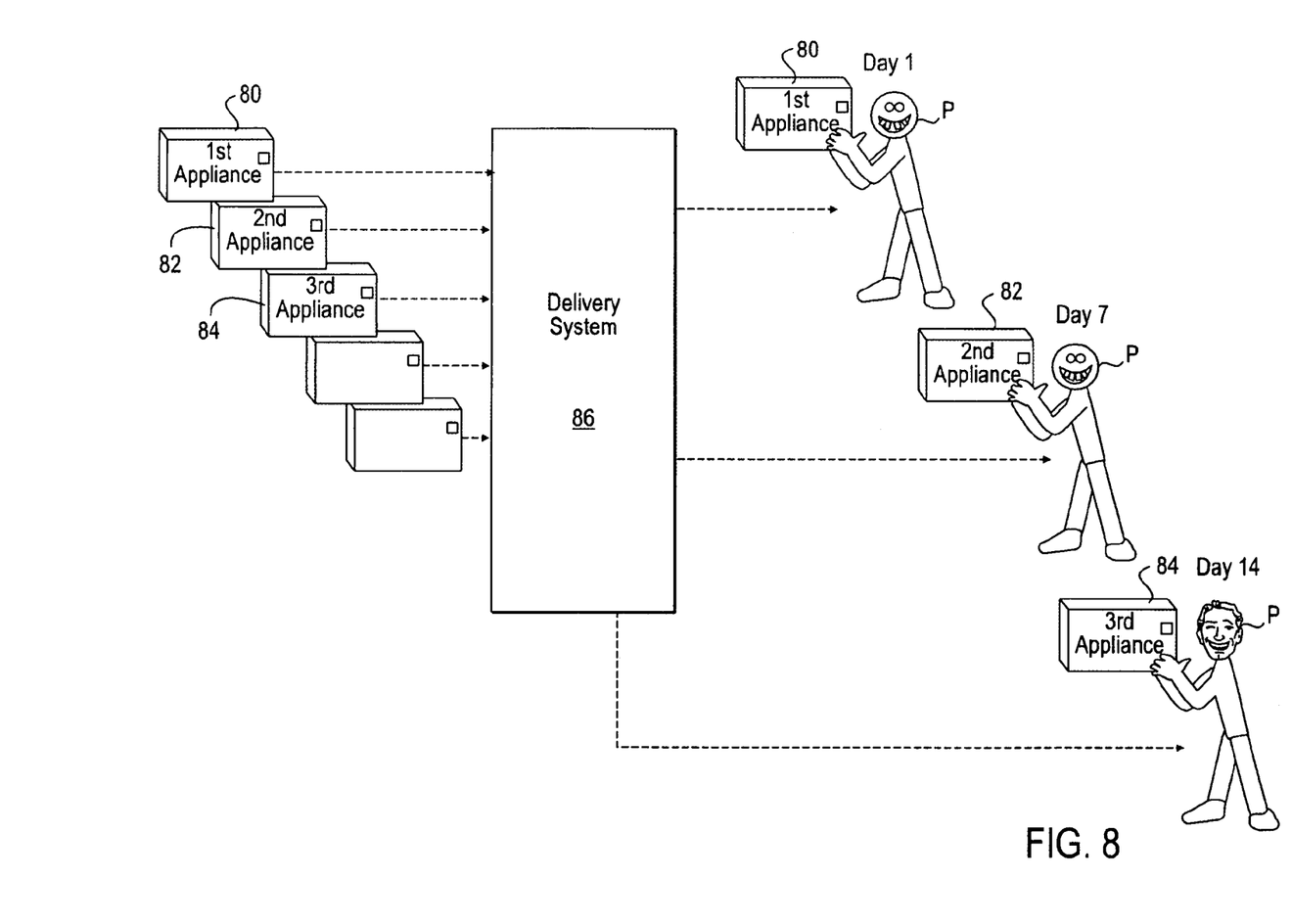
FIG. 8 illustrate an embodiment of a method of delivering appliances in a desired order.

Alternatively or in addition, the patient may be provided with individual appliances in the order in which they should be used. To provide such ordering while allowing the appliances to be stored and distributed to the patient in the correct sequence with minimal attention from the orthodontic practitioner, a method may be used in which the appliances are delivered by mail in a specific sequence. FIG. 8 illustrates an embodiment of such a method. As shown, the appliances 10 are individually packaged so that a first package 80 contains a first appliance, a second package 82 contains a second appliance, a third package 84 contains a third appliance, etc. The packages 80, 82, 84 are sent through the mail or any delivery system so that they are delivered to the patient P according to a desired schedule. For example, the first package 80 is delivered to the patient P at day 1, the second package 82 is delivered at day 7, the third package 84 is delivered at day 14, etc. It may be appreciated that the individual packages may alternatively be comprises of series of appliances, such as subsets of the entire series of the treatment plan. In such a case, the patient P is delivered a package of appliances 10 at each interval, wherein each package includes a series of appliances. The series may itself also be ordered by any given system, including any of those mentioned above.

Figure 9:
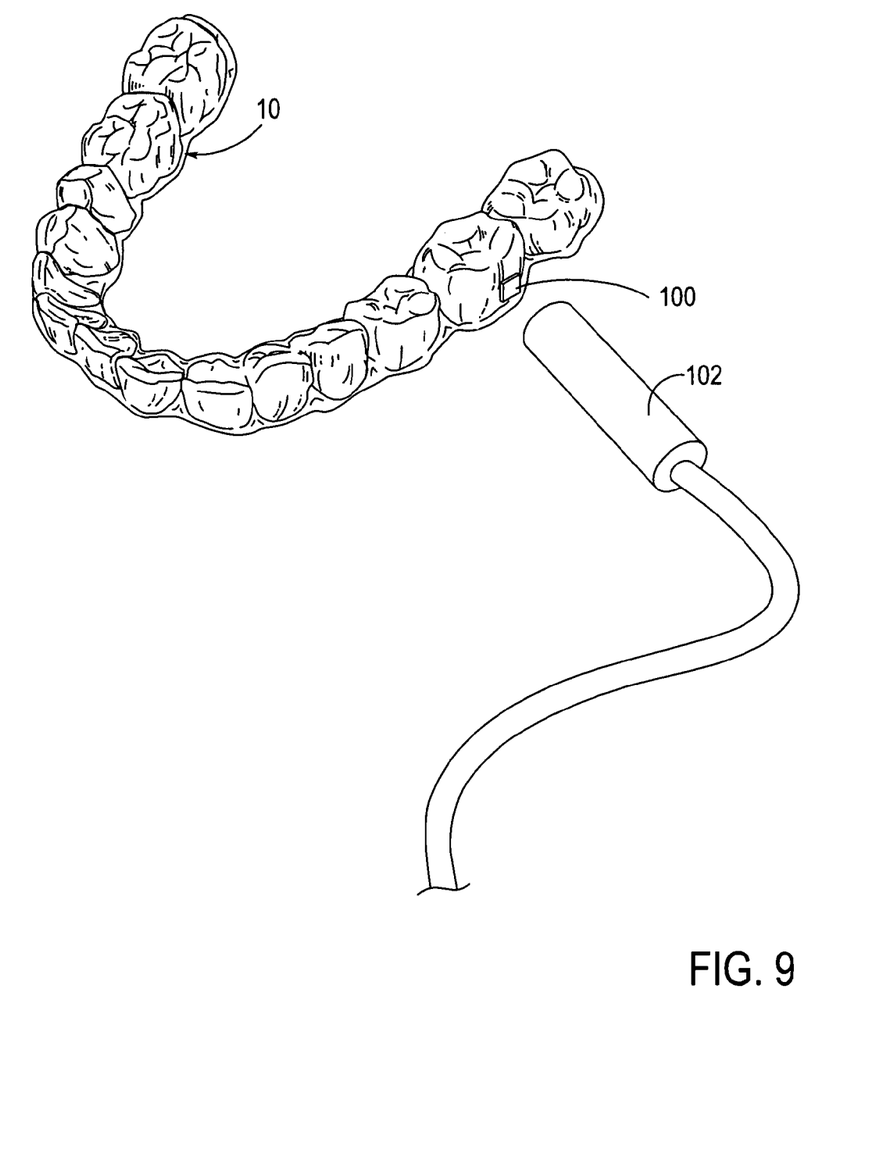
FIG. 9 illustrates an appliance which includes a readable element embedded in the appliance.

FIG. 9 illustrates one appliance 10 of a series of appliances wherein the appliance 10 includes a readable element 100 embedded in the appliance 10. Alternatively, the readable element 100 may be affixed to the appliance 10 or to a package enclosing the appliance. The readable element 100 may comprise a chip, a bar code or other element that is computer readable, including identification by wireless means, including radiofrequency (rf) identification. When a reader 102 passes over the element 100, the reader 102 translates the information into a word, symbol or other identifying feature. When translated into a word, the word may include, "first", "second", "third", or "last" to name a few. Also, the word may be in any language, including English, Spanish, French, German, Japanese, etc. The word or identifying feature may be auditory, such as a recording or generation of a spoken voice, or visual, such as a print display. Alternatively, the feature may be transmitted by tactile means, such as by vibration.

Figure 10:
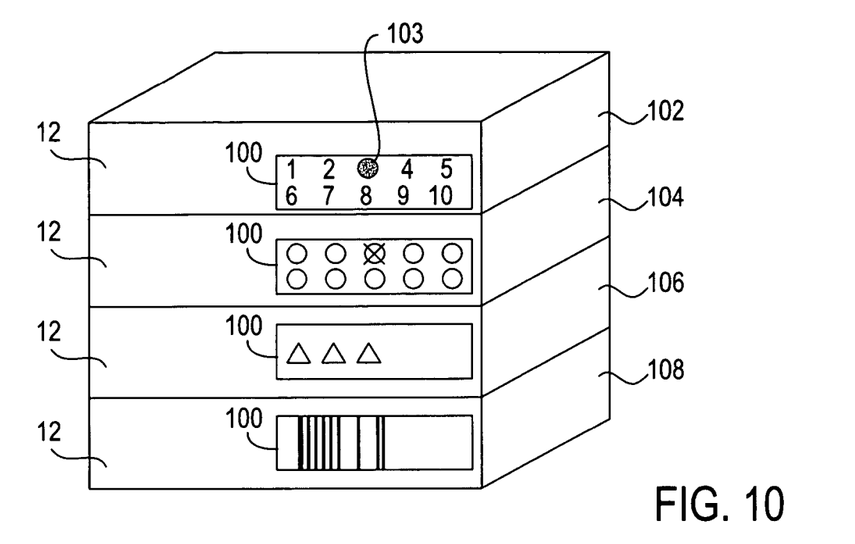
FIG. 10 illustrates a series of packages 12, each having a label which includes at least one non-numeric indicia.

FIG. 10 illustrates a series of packages 12, each package 12 including at least one appliance 10. Affixed to or incorporated in each package 12 is a label 100. The label 100 includes at least one non-numeric indicia. For example, a first package 102 shows a label 100 having a series of numbers wherein one number is marked, in this case stamped with a colored dot 103. This indicates which appliance 10 the first package 102 contains in the treatment sequence. It may be appreciated that the number can be marked with any symbol by any method, including removing the number by erasure, punch-out or notching. It may also be appreciated that other symbols may be used other than numbers, wherein one of the symbols is marked. This is illustrated in a second package 104 which shows such a label 100. A third package 106 shows a label 100 having a series of symbols, such as shapes, in this case, triangles 120. The symbols themselves or the color, number, or arrangement may indicate which appliance 10 the third package 106 contains in the treatment series. It may be appreciated that such symbols may include stripes, as illustrated on a fourth package 108 which shows such a label 100. The stripes may be human readable or computer readable, such as a barcode.

Figure 11:
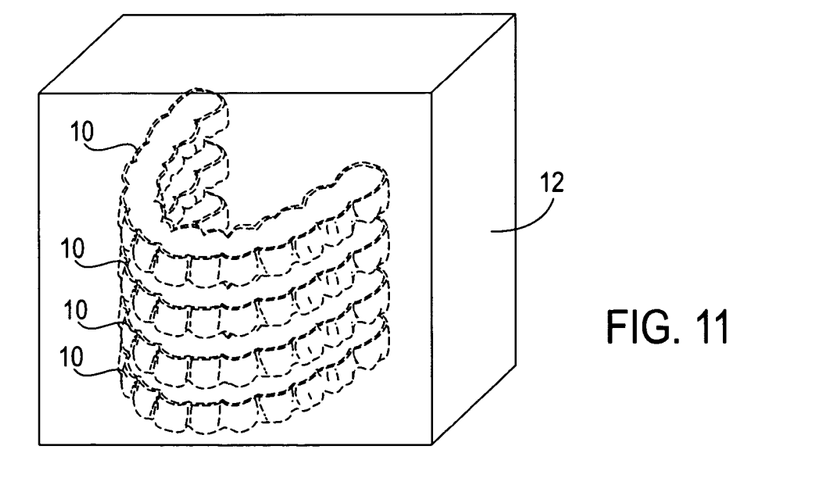
FIG. 11 illustrates a package of dental appliances of the present invention.

FIG. 11 illustrates an embodiment of a package of dental appliances comprising a package 12 including a plurality of dental appliances 10 positioned in an arrangement within the package 12 which indicates an order of usage. In this embodiment, the arrangement comprises stacking of the appliances.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A system of dental appliances comprising:
a plurality of dental appliances wherein at least some of the plurality include a non-numeric indicia designating an order in which each of the at least some of the plurality are to be worn by a patient to provide dental treatment, each of the plurality of dental appliances comprising a polymeric shell having cavities shaped to receive and resiliently reposition teeth from one arrangement to a successive arrangement, and each of the polymeric shells having at least one terminal tooth cavity, wherein the indicia comprises a terminal tooth cavity of differing length in each of the polymeric shells.

2. A system of dental appliances comprising:
a plurality of dental appliances wherein at least some of the plurality include a non-numeric indicia designating an order in which each of the at least some of the plurality are to be worn by a patient to provide dental treatment, each of the plurality of dental appliances comprising a polymeric shell having cavities shaped to receive and resiliently reposition teeth from one arrangement to a successive arrangement, and each of the polymeric shells having a height, wherein the indicia comprises a different height in each of the polymeric shells.

\* \* \* \* \*

UNITED STATES PATENT AND TRADEMARK OFFICE
CERTIFICATE OF CORRECTION

PATENT NO. : 7,648,360 B2
APPLICATION NO. : 10/612239
DATED : January 19, 2010
INVENTOR(S) : Eric Kuo It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 678 days.

Signed and Sealed this

Sixteenth Day of November, 2010

David J. Kappos
*Director of the United States Patent and Trademark Office*